United States Patent [19]
Keith et al.

[11] Patent Number: 5,104,796
[45] Date of Patent: Apr. 14, 1992

[54] HIGH TITER PRODUCTION OF HUMAN SOMATOMEDIN C

[75] Inventors: Paula M. Keith; Wendy Cain, both of Terre Haute, Ind.

[73] Assignee: International Minerals & Chemical Corp., Northbrook, Ill.

[21] Appl. No.: 34,847

[22] Filed: Apr. 6, 1987

[51] Int. Cl.$^5$ .................. C12P 21/02; C07K 13/00; C12N 1/21; C12N 15/03; C12N 15/18

[52] U.S. Cl. .................. 435/69.4; 435/69.1; 435/320.1; 435/172.3; 435/252.33; 435/71.2; 536/27; 530/399; 935/33; 935/38; 935/39; 935/44; 935/61; 935/43; 935/73

[58] Field of Search .................. 435/68, 70, 91, 172.3, 435/320; 514/12; 430/300, 303, 399

[56] References Cited

U.S. PATENT DOCUMENTS

| | | | |
|---|---|---|---|
| 3,926,737 | 12/1975 | Wilson et al. | 195/108 |
| 4,762,784 | 8/1988 | Keith et al. | 435/70 |
| 4,769,361 | 9/1988 | Burleigh et al. | 435/70 |
| 4,788,144 | 11/1988 | McMullen | 435/70 |
| 4,831,120 | 5/1989 | Aviv et al. | 530/399 |

FOREIGN PATENT DOCUMENTS

| | | |
|---|---|---|
| 0103495 | 3/1984 | European Pat. Off. |
| 8500831 | 2/1985 | World Int. Prop. O. |

OTHER PUBLICATIONS

Nucleic Acids Research, vol 13(6), Mar. 25, 1985, Table of Contents.
Peters et al., 1985 Expression of a biologically active somatomedin-C/insuline-like growth factor I, Gene 35, 83-89.
Buell et al., 1985 Optimizing expression in *E. coli* of a synthetic gene encoding somatomedin-C (IGF-I), Nic. Acids Res. 13, 1923-1938.
Bauer and Shiloach, Maximal Exponential Growth Rate and Yield of *E. coli* Obtainable in a Bench-Scale Fermentor, Biotechnology and Bioengineering, 16, 933 (1974).
Shiloach and Bauer, High-Yield Growth of *E. coli* at Different Temperatures in a Bench-Scale Fermentor, Biotechnology and Bioengineering, 17, 227 (1975).
Bauer and White, Pilot Scale Exponential Growth of *Escherichia coli* W to High Cell Concentration with Temperature Variation, Biotechnology and Bioengineering, 18, 839 (1976).
Rinderknecht and Humbel, The Amino Acid Sequence of Human Insulin-like Growth Factor I and Its Structural Homology with Proinsulin, *J. Biol. Chem.*, 253(8), 2769 (1978).
Buell et al., Optimizing the Expression in *E. coli* of a Synthetic Gene Encoding Somatomedin-C (IGF-I), *Nucleic Acid Res.*, 13, 1923, (1985).
Rotwein et al., Organization and Sequence of the Human Insulin-Like Growth Factor I Gene, *J. Biol. Chem.*, 261(11), 4828 (1986).

Primary Examiner—Elizabeth C. Weimar
Assistant Examiner—Christopher S. F. Low
Attorney, Agent, or Firm—Wendell Ray Guffey; Thomas L. Farquer

[57] ABSTRACT

A high titer fermentation process using transformed *Escherichia coli* cells carrying a plasmid containing DNA which codes for Somatomedin C is disclosed. Titers of about 900-1000 mg/L have been obtained using the method of the present invention; about two times the titer of prior art processes.

18 Claims, 2 Drawing Sheets

HIGH TITER PRODUCTION OF HUMAN SOMATOMEDIN C

This invention relates generally to the production of Somatomedin C using recombinant microorganisms and particularly to a high titer fermentation process using transformed *Escherichia coli* (*E. coli*) cells carrying a plasmid containing DNA which codes for Somatomedin C.

Somatomedin C (SmC), also known as insulin-like growth factor one (IGF-1), is a naturally occurring 70 amino acid polypeptide found in plasma and serum. SmC plays a fundamental role in the growth process as a mediator of somatotropin. SmC has been prepared by extracting small quantities of the protein from large quantities of plasma or serum (Phillips et al., *New England J.Med.*, 302:371-80 (1980)); by binding the protein to monoclonal antibodies produced using hybridoma technique (Laubli et al., *F.E.B.S. Letters*, 49:109-112 (1982)); and by chemically synthesizing the protein (Li et al., *PNAS (USA)*, 80:2216-20 (1983)). All these techniques generate the protein in small, non-commercial quantities and produce an impure protein product.

The production of commercial quantities of many valuable proteins such as SmC using recombinant DNA technology is well known in the art. Expression of these proteins is achieved by cloning the DNA coding sequence for the protein into multi-copy plasmids having strong promoters and other sequences which facilitate the expression of the heterologous protein. Using recombinant DNA technology to produce commercial quantities of a desired protein such as SmC often involves transforming several host cell strains and comparing the strains to determine which strain expresses the desired protein in the highest yield. Additionally, fermentation process conditions such as temperature, pressure, nutrients, fermentation mediums, oxygen supply, and the like are often varied in an attempt to increase the yield to a commercially feasible level.

SmC has been produced using recombinant DNA technology. However, the plasmid vectors employed have generally coded for fusion proteins and the yield of purified, active SmC has been small. WO 85/00831 discloses a manufactured gene coding for natural and mutant SmC, a microorganism transformed with a vector containing the SmC gene fused to β-galactosidase, and a process for producing SmC using the transformed microorganisms. The amount of SmC produced by the process was, however, too small to provide the quantities needed for further research and commercial development. Buell et al., *Nucleic Acids Research*, 13(6):1923 (1985) discloses several *E. coli* cell strains containing DNA encoding SmC. The expression of SmC is controlled by the bacteriophage $P_L$ promoter and a temperature-sensitive repressor encoded by the cI857 gene. Also, disclosed is an *E. coli* cell strain having mutations in the lon and htpR "heat shock genes." Generally, the transformed cells were grown overnight at 28° C. and the expression of the protein was induced by raising the temperature to 42° C.

Using these methods, titers of about 300-500 mg/L were obtained in shake flask volumes of less than 100 mls broth.

Although these techniques successfully produced SmC, there exists a continuing need for new processes which can increase the titer and therefore the amount of SmC recovered from fermentation processes involving recombinant microorganisms.

SUMMARY OF THE INVENTION

It is, therefore, an object of the present invention to provide a high titer fermentation process for producing SmC from recombinant microorganisms.

It is another object of the present invention to provide a high titer fermentation process for producing SmC from recombinant microorganisms transformed with expression vectors containing genes encoding for SmC and a temperature-sensitive repressor protein.

These and other objects are achieved using a higher titer fermentation process for producing SmC from recombinant *E. coli* cells transformed with a vector containing DNA encoding for SmC. SmC expression is controlled by a temperature-sensitive repressor encoded on a second plasmid which has also transformed the *E. coli* cells. Using the present process, titers of about 900–1000 mg/L have been obtained; about two times the titer of prior art processes. This fermentation process has been successfully scaled-up to commercial volumes of 300 liters.

According to the present invention, a process for producing SmC comprises inoculating an aqueous fermentation medium with a transformed *E. coli* strain containing an expression vector which directs the expression of SmC under the control of a phage lambda promoter and an expression vector which directs the expression of the cI857 temperature-sensitive repressor protein. The transformed *E. coli* strain is grown in the fermentation medium for an initial growth period during which the level of dissolved oxygen in the medium is maintained at from about 20% to about 60% of saturation and the temperature of the medium is maintained between about 26° C. and 30° C. The initial growth period is followed by an induction period during which SmC synthesis is induced by raising the fermentation medium temperature to about 40° C. to inactivate the temperature-sensitive cI857 protein while maintaining the dissolved oxygen level in the medium at from about 10% to 40% saturation. The SmC produced by the above process is subsequently recovered from the *E. coli* cells by means well known in the art.

Other objects, advantages, and novel features of the present invention will become apparent from the following detailed description of the invention.

DETAILED DESCRIPTION OF THE INVENTION

Figure 1:
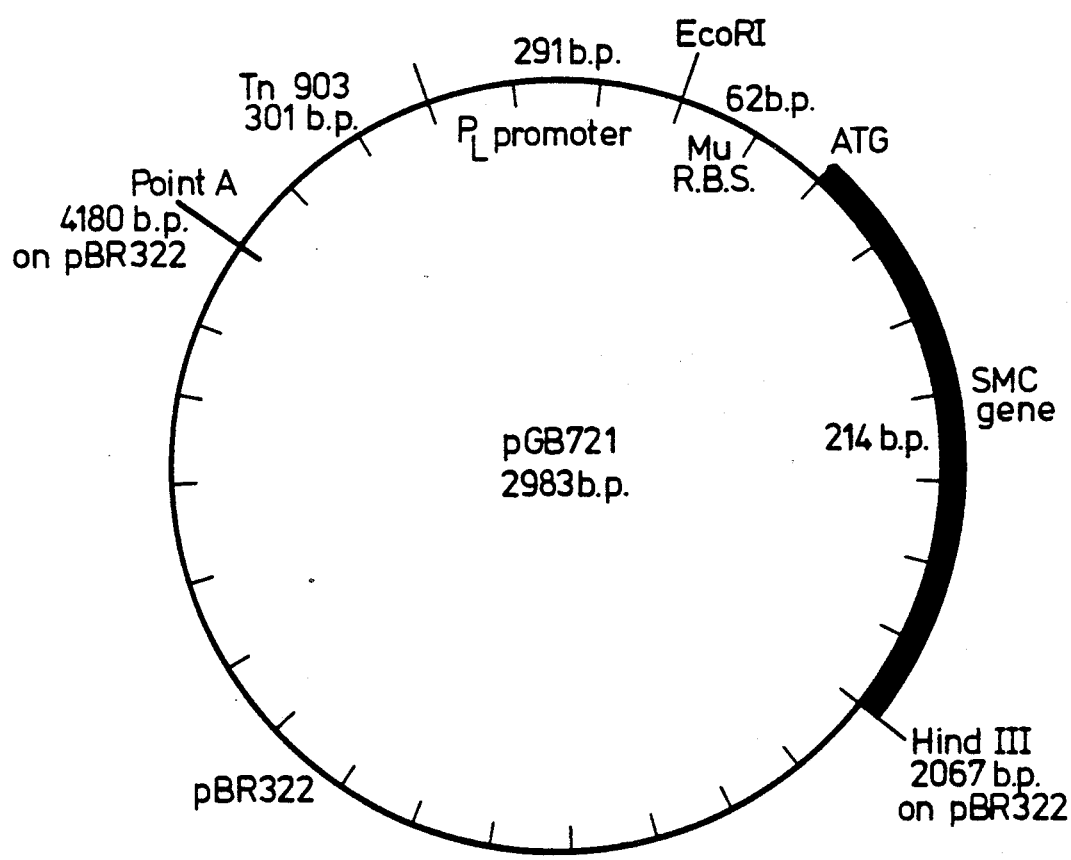
FIG. 1 is a representation of the salient features of plasmid pGB721, a SmC expression vector which can be used in the process of the present invention.

According to the present invention, a high titer process for producing SmC comprises inoculating an aqueous fermentation medium with a transformed *E. coli* strain containing an expression vector which directs the expression of Somatomedin C under the control of a phage lambda promoter-operator and an expression vector which directs the expression of the cI857 temperature-sensitive repressor protein; growing the transformed strain in the fermentation medium for an initial growth period during which the level of dissolved oxygen in the medium is maintained at from about 20% to 60% of saturation and the temperature of the medium is maintained at from about 26° to 30° C.; raising the temperature of the fermentation medium to about 40° C. to inactivate the temperature-sensitive protein and initiate an induction period during which Somatomedin C is expressed; allowing the transformant strain to express SmC for the remainder of the induction period, during which the level of dissolved oxygen in the medium is maintained at from about 10% to about 40% of saturation; and recovering the Somatomedin C peptide from the transformed cells by means well known to skilled artisans.

The expression vector which directs SmC expression in the process of the invention can be any suitable SmC-encoding plasmid in which SmC expression is directed by a regulatory region comprising a promoter-operator region derived from bacteriophage lambda, preferably the lambda $P_L$ promoter-operator region. The regulatory region may also contain a Shine-Dalgarno (Ribosomal binding) region, which is preferably derived from bacteriophage mu.

The SmC-encoding sequence, which is operably fused to the regulatory region, comprises a DNA sequence encoding a polypeptide having the amino acid sequence of SmC or a biologically active fragment or analog thereof. As used herein, the term "SmC" is defined herein to include all recombinant proteins having SmC activity including mutein SmCs having deleted, inserted, substituted, or otherwise modified sequences. Preferably, the SmC-encoding plasmid encodes a polypeptide corresponding in amino acid sequence to α-methionyl-human SmC.

Advantageously, the plasmid also carries a gene encoding a selectable marker, e.g., an antibiotic resistance gene, for selection of cells transformed by the plasmid.

The preferred expression vector for use in the present invention is plasmid pGB721. Plasmid pGB721 ($P_L$-mu-SmC), represented in FIG. 1, encodes a α-methionyl-SmC polypeptide. Expression of the SmC-encoding sequence is controlled by a regulatory region comprising the phage $P_L$ promoter-operator, a Shine-Dalgarno region derived from bacteriophage mu, and an initiation codon (ATG) adjacent and 5' to the SmC sequence. The plasmid also carries a gene for ampicillin resistance. The method for producing pGB721 and its characteristics are disclosed in Buell, Optimizing the expression in *E. Coli.* of a synthetic gene encoding Somatomedin-C (IGF-I), *Nucleic Acid Res.*, 13, 1923–38 (June 1985).

Referring to FIG. 1, the somatomedin C gene was cloned on plasmid pP$_L$C24 (Gene, 15: 81–93, 1981) which is a derivative of pBR322 (G. Sutcliffe, Cold Spring Harbor Symposia 1978). Point A on the plasmid is nucleotide 4180 in the Sutcliffe sequence. Plasmid pBR322 then continues counterclockwise to the Pvu II recognition site at nucleotide 2067 of the pBR322 sequence. Clockwise from point A is a 301 base pair (b.p.) fragment from Tn903 which was inserted with the 291 b.p. $P_L$ promoter. An EcoR I restriction site divides the promoter from a mu sequence which supplies the ribosome binding site up to the initiating ATG codon. The six codons following the ATG are GGT CCT GAA ACT TTG and TGC. This is followed by 192 b.p. which code for amino acids 7–71 of somatomedin C. A linker converts the Pvu II site to a Hind III site.

Figure 2:
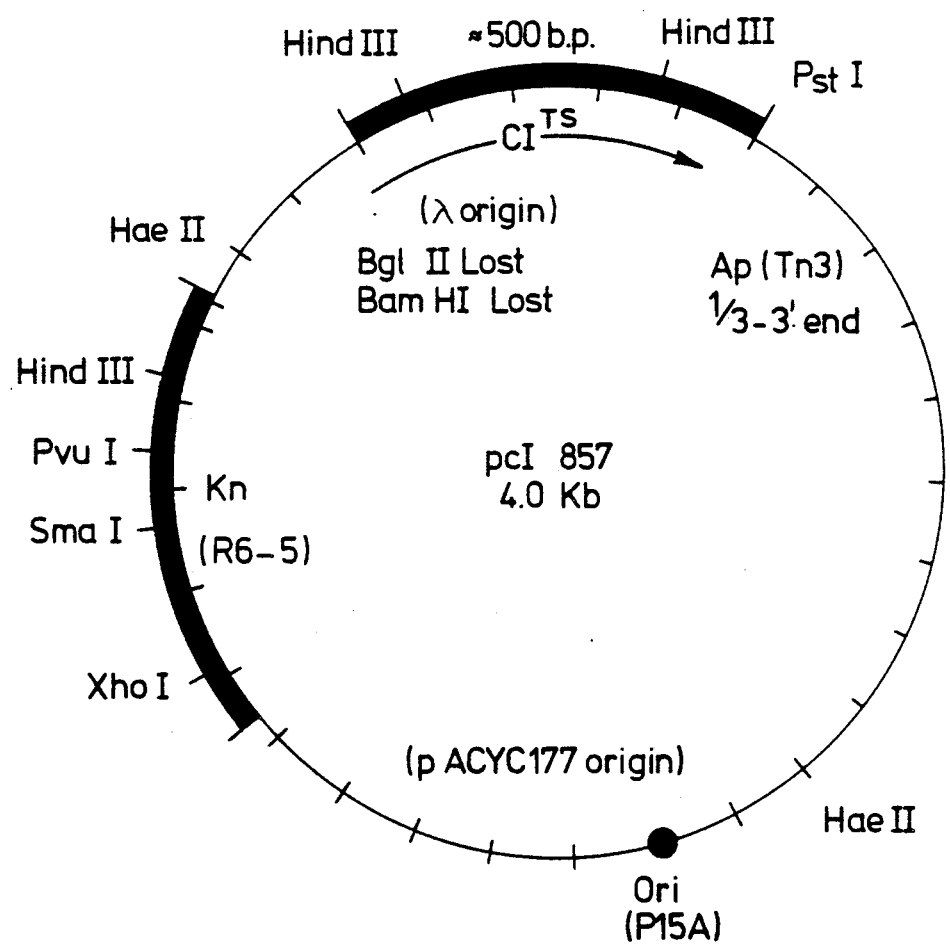
FIG. 2 is a representation of the salient features of plasmid pcI857, an expression vector which encodes a temperature-sensitive repressor used to control SmC production in the process of the present invention.

The expression vector which directs the expression of the cI857 temperature-sensitive repressor protein according to the present invention contains a gene encoding a repressor protein which interacts with the operators of phage 1 gene regulatory regions, including the $P_L$ operator, to prevent gene transcription from the promoter in the regulatory region. Plasmid cI857, represented in FIG. 2, is a multicopy plasmid which encodes the cI857 temperature-sensitive repressor and also carries a kanamycin resistance gene.

cI857 encoded repressor protein has been used to regulate synthesis of desired proteins encoded by recombinant vectors in various transformant strains. See for example, C. Queen *J. Mol. and Appl. Genetics*, 2:1 (1983); H. Kupper European Patent Application Publication No. 0 076 037; and G. Buell European Patent Application Publication No. 0 103 395. These references describe the use of the cI857 repressor to regulate synthesis of a protein encoded on a recombinant vector. The cI857 gene is either carried on the vector carrying the gene for the desired protein along with the promoter-operator region directing its expression or on a separate plasmid transformed into the host cells. Synthesis of the desired protein is repressed by cultivating the transformant host cells at temperatures between 28° C. and 32° C. until the desired cell density was reached. The cI857 repressor is subsequently inactivated, thus inducing synthesis of the desired protein, by raising the temperature to 40°–43° C. for the remainder of the cultivation period.

The cI857 gene is used in the process of the invention to control SmC synthesis. The cI857 gene may be carried on the host cell chromosome, on the SmC-encoding plasmid, or on a second plasmid. In a preferred embodiment of the invention, a second plasmid which directs expression of the cI857 repressor protein is transformed into the host strain along with the SmC-encoding plasmid. The cI857 repressor interacting with the $P_L$ promoter-operator is inactivated to some degree at temperatures as low as 37° C., as evidenced by inclusion body formation (indicating SmC synthesis) in shake flask cultures. The best results were achieved, however, by inactivating the cI857 repressor by raising the temperature to 40° C. and maintaining the 40° C. for the remainder of the fermentation.

The transformant host cells of the present invention may be any transformable *E. coli* strain with mutation that affect intracellular protease levels. Strains with protease impairment include derivatives with mutations in the gene lon and htpR.

A preferred transformant strain for use in the process of the invention is *E. coli* SG936 ($P_L$-mu-SmC and pcI857). This strain is a double mutant (i.e. is lon⁻ and htpR⁻), so protease levels are low, allowing production of peptides like SmC. *E. coli* SG936 cells transformed with both plasmids were selected by growth in Luria broth supplemented with both ampicillin and kanamycin using procedures well known in the art; e.g. procedures similar to those described in EPO 0 103 395. *E. coli* SG936 ($P_L$-mu-SmC and pcI857) has been deposited with the American Type Culture Collection, Rockville, Md. and assigned accession number 53551 (ATCC 53551). Applicants have directed that the deposited microorganism containing the plasmids be freely available to the general public upon issuance of a U.S. Patent citing the assigned accession number. It will be appreciated, however, that the process of the invention is equally applicable to obtain high level production of SmC using other transformant strains in which SmC expression is under control of the cI857 gene encoded repressor protein.

The transformant strain is used to inoculate an aqueous medium contained in a fermentor. The aqueous fermentation medium can be any medium suitable for supporting high density growth of *E. coli*. The medium contains a carbon source, a nitrogen source, salts, and any other nutrients required for cell growth. Suitable carbon sources include, among others, glycerol and hydrated glucose (available commercially as CERELOSE® brand of glycerol and hydrated glucose). Suitable nitrogen sources include, among others, acid hydrolysates of casein (commercially available as HyCase® brand of acid hydrolysates of casein; enzymatic hydrolysates of casein (NZ Amine A, Casatone, Tryptone); Amberex 510; vegetable derived hydrolyzed proteins (soybean peptones, hydrolyzed corn gluten, cottonseed peptone); meat peptones; and yeast extracts. The foregoing list of carbon and nitrogen sources is merely exemplary of known, commercially available sources. A suitable fermentation medium for use in the present invention is shown in Table 4. Other suitable carbon and nitrogen sources will be readily apparent to those skilled in the art.

Any components required for retention of plasmids by host cells are added to the medium. For example, the antibiotics ampicillin and kanamycin are added when the transformant strain *E. coli* SG936 ($P_L$-mu-SmC and pcI857) is grown in a fermentor according to the present invention.

The fermentor is inoculated with a culture of the transformant strain. Advantageously, the culture will have been previously incubated at about 28° C. for between 8 and 24 hours (or until the $A_{550}$, i.e., the absorbance at 550 nanometers, of the culture is between 4 and 10) with agitation, for example, at 200 rpm. Preferably, the culture is incubated at about 28° C. for about 14 to 20 hours, or until the $A_{550}$ is between 4 and 6. The culture can be grown in any suitable medium, for example, Luria broth. The volume of culture used to inoculate the fermentor is between 0.5 and 5.0% (vol/vol), preferably about 2.0% (vol/vol).

According to the present invention, the high titer fermentation is conducted in two phases. Following inoculation of the fermentation medium with the transformant strain, an initial growth period is conducted during which the level of dissolved oxygen in the medium is maintained at from about 20% to 60% saturation, preferably at about 50% saturation. This may be accomplished by feeding ambient air into the fermentor at a rate sufficient to maintain the dissolved oxygen concentration at the desired level, while also agitating the fermentation medium by any suitable mechanical means. Feeding ambient air at a rate of 0.8 to 1.2, preferably about 1.0, volume of air (STP) per volume of liquid per minute with agitation at 800 to 1200 rpm, preferably about 1000 rpm, is suitable. The agitator is driven by a motor which preferably provides a power input of about 0.5 to 2.0 horsepower per 100 gallons of fermentation medium.

The temperature of the medium during the initial growth period is any temperature at which *E. coli* growth is supported while the cI857 repressor protein is active and SmC expression in the transformant strain is therefore repressed. During the initial growth period, the temperature is preferably held between 26° C. and 30° C., most preferably at about 28° C.

The initial growth period is continued until cell density reaches an $A_{550}$ of about 25–35, preferably about 30. This commonly occurs at about 14 to 20 hours after inoculation of the fermentation medium.

At this point, the second fermentation phase, an induction period, is begun. The temperature of the fermentation medium is raised to about 40° C. and held there for about 3 to 8 hours, preferably about 4 to 5 hours. The higher temperature inactivates the cI857 repressor protein and induces expression of SmC in the transformant microorganisms.

The dissolved oxygen level in the medium is maintained at from about 10% to 40% of saturation during the induction period. Any suitable means of aeration and agitation can be used to maintain this dissolved oxygen level. In a preferred embodiment of the invention, ambient air is fed at a rate of 0.8 to 1.2, preferably about 1.0, volumes of air (STP) per volume of liquid per minute, and the medium is agitated at 800 to 1200 rpm, preferably about 1200 rpm. The agitator is driven by a motor which preferably provides a power input of about 0.5 to 2.0 horsepower per 100 gallons of fermentation medium. Since the rate of oxygen consumption is increased during the induction period, it is preferred to supplement the oxygen present in the ambient air source by feeding oxygen into the fermentor in order to maintain the desired dissolved oxygen level. Any conventional means of providing oxygen to the fermentation medium may be employed. For example, a sparger which is connected to an oxygen source may be inserted directly into the medium or oxygen may be added to the ambient air being fed into the fermentor.

The induction period is continued until cell density reaches an $A_{550}$ of about 35 to 45, preferably about 40. These cell densities are commonly reached at about 3 to 8 hours after the start of the induction period. Fermentation parameters indicating that cell growth and SmC expression are complete include: (1) a significant decrease in oxygen demand (2) no further increase in cell density ($A_{550}$ values) and (3) NaOH (base) utilization for pH control stops. Nutrients which are depleted from the fermentation medium during cell growth are replenished by any of the methods known in the art. Nutrients may be fed continually or in portions during the fermentation. Preferably, nutrients are added to the fermentation medium just before the temperature is raised to begin the induction period, usually about 14 to 20 hours after inoculation.

The nutrients to be added will depend on the composition of the fermentation medium chosen, but will generally include a carbon source and a nitrogen source. Advantageously, the feedings comprise about equal amounts by weight of glycerol, yeast extract, and enzymatic casein hydrolysate, preferably NZ Amine A and A510 yeast extract. Preferably, the feeding comprises a total of about 45–60 grams of the combined nutrients per liter of medium in the fermentor. Excellent results were achieved by adding about 200 grams each of NZ Amine A, A510 yeast extract, and glycerol in one liter of water to 9 liters of fermentation medium just before the temperature was raised to begin the induction period.

The pH of the fermentation medium used in the present process is maintained at from about 6.5 to 7.0 using any suitable base, preferably NaOH.

Any conventional fermentation equipment known in the art can be used, provided there are means for controlling the medium temperature, agitating and aerating the medium, controlling the pH, and adding oxygen to the intake air.

Typical fermentation parameters useful in the present invention are shown in Table 2. These parameters are particularly useful with the preferred E. coli strain SG936.

The SmC produced by the transformant strain may be recovered by any suitable means known in the art. Cells may be harvested from the fermentation medium by, for example, centrifugation. Cells are subsequently lysed by enzymatic, chemical or mechanical means, for example, using sonication, a French press, or treatment with such agents as lysozyme and detergents such as Triton-X-100. SmC may be purified from the cell lysate by any suitable protein purification method, including affinity chromatography, selective precipitation from a solution of a salt such as ammonium sulfate, ion exchange chromatography, isoelectric focusing, or any combination of these or other suitable methods.

The high titer fermentation process of the present invention has yielded 900–1000 mg/L of SmC. It has successfully been duplicated at commercial scale fermentor volumes of 300 liters. This is about a two fold increase over the reported titers of 400–500 mg/L SmC obtained with prior processes at the small volume scale and about a two fold increase based on estimates from SDS-PAGE gels for small scale productions.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Comparative fermentation studies were performed with E. coli strains HB101 and SG936 transformed with pGB721 and pCI857 plasmid DNAs. Strain SG936 has chromosome mutations in the loci lon and htpR which result in lower levels of intracellular proteases, compared to lon+, htpR+ E. coli strains such as HB101. It was hypothesized that higher levels of SmC could accumulate in protease-impaired strains such as SG936 compared to expression in lon+, htpR+ strains such as HB101 where proteolytic degradation could result in lower production levels.

To compare SmC expression in wild type versus protease impaired E. coli, bacterial strains were cultivated at 28 C. in a Microgen fermentor containing 9 liters of complex media. At a cell density $A_{550}=36$, fresh nutrients were added and the fermentor temperature was raised to 42 C. for induction of α-methionyl SmC.

Unlike E. coli HB101, the lon−, htpR− host SG936 produced a refractile inclusion body of aggregated SmC that was visible at 1,000× magnification approximately 2–4 hours after induction. Although the amount of biomass produced by E. coli SG936 (517 g wet wt. whole cells) was less than that of strain HB101 (885 g wet wt.), the amount of detectable SmC was significantly greater in SG936 as estimated by gel permeation chromatographic analysis or by SDS-PAGE. The comparative expression of SmC in E. coli HB101 versus SG936 is summarized in Table 1.

Somatomedin C was present in SG936 cells as an aggregate that was easily recoverable by centrifugation from broken bacterial cells. To collect SmC inclusion bodies, bacteria were treated with lysozyme and lysed by 4 passes through a Manton-Gaulin homogenizer at a pressure of 6,000 psi. SmC inclusions were collected by centrifugation at 14,300×g for 20 min and the crude pellet was resuspended in 500 ml of Tris buffer (100 mM Tris-Cl pH 7.5, 0.5 mM DTT, 0.5 mM PMSF). The unwashed inclusions were frozen at −80 C. for use in subsequent recovery and purification of biologically active SmC.

TABLE 1

| | Expression of α-methionyl SmC in E. coli SG936 versus HB101 | | | |
|---|---|---|---|---|
| E. coli strain | Relevant Genotype | Presence of Aggregated SmC in Inclusion body | Detectable SmC by SDS-PAGE | Estimated SmC by GPC |
| HB101 | lon+, htpR+ | − | − | <100 |
| SG936 | lon−, htpR− | + | + | 500 |

EXAMPLE 2

Expression of Somatomedin C is controlled by a temperature-sensitive repressor encoded by the lambda-CI857 gene. In many lon+, htpR+ E. coli strains such as HB101, the optimum temperature for induction of expression is 42°–45° C. Because strain SG936 has an impairment in the locus htpR which regulates the heat shock response in E. coli, the ability of this strain to grow and produce SmC during elevated temperature induction was studied. Growth, as measured by an increase in optical density ($A_{550}$) and SmC production as estimated by GPC were compared at induction temperatures of 40° and 42° C. The results are summarized in Table 2. Repeat studies both in shake flask and at the 10-liter fermentor level, indicated higher expression levels of SmC when 40° C. was used as the induction temperature, rather than 42°–45° C. which is the optimum for expression of foreign proteins in E. coli HB101.

TABLE 2

| | Induction of α-methionyl SmC in E. coli SG936 at the 10-liter Scale | | | |
|---|---|---|---|---|
| Experiment # | Temperature | Initial $A_{660}$ | Final $A_{660}$ | GPC estimate SmC level (mg/l) |
| I. | 40 | 40 | 48 | 1,000 |
| | 42 | 39 | 42 | 450 |
| II. | 40 | 40 | 51 | 1,000 |
| | 42 | 17 | 24 | 500 |

EXAMPLE 3

Several growth and induction media were evaluated for their effects on SmC production in E. coli SG936 transformed with pCI857+pGB721. Varying amounts of an enzymatic hydrolysate of casein (NZA-A) an acid casein hydrolysate (Hycase) and a yeast extract (Amberex 510) were added to basal media. SmC production was evaluated by 12–20% linear gradient gels and by gel permeation chromatography. Supplementation of the basal medium with yeast extract was shown to stimulate growth of E. coli SG936. Similarly, addition of yeast extract to induction media resulted in a doubling in the amount of SmC produced per liter of culture as shown in Table 3.

TABLE 3

Effect of Nitrogen Source on Growth and Reduction of *E. coli* SG936

| Fermentor # | N source in Growth Media | A$_{550}$ at Induction | N source in Induction Media | A$_{550}$ Final | SmC titer |
|---|---|---|---|---|---|
| SmC 28 | NZA | 24 | NZA | 33 | 500 |
| SmC 33 | NZA + YE | 40 | NZA + YE | 48 | 1000 |

YE = yeast extract

EXAMPLE 4

Media optimization studies in shake flasks and at the 10-liter fermentation scale revealed that yeast extract, added to basal media, could substitute for casein hydrolysate in supporting good growth (A$_{550}$=30–40) of *E. coli* SG936. Highest titers of SmC (1,000–1,200 mg/l) were produced when combinations of yeast extract and casein hydrolysate were used in induction media. Similarly, a consistent fermentation process with reproducible SmC production is assured when an enriched seed medium is used to prepare primary inocula for fermentation procedures.

Because *E. coli* SG936 contains chromosomal mutations in two loci (lon and htpR), consistency in production of SmC by fermentation is ensured by routinely testing for revertants prior to preparation of primary seed cultures. For culture preservation, cells of *E. coli* SG936 are preserved in 10% glycerol at −80 C. or in liquid nitrogen. Stock cultures are streaked on LB agar and plates are incubated at 30 C. and 42 C. to test for revertants. A single colony isolate is picked from plates incubated at 30 C. and used to inoculate primary seed flasks of seed media.

The formulations used in the preparation of inocula, growth of SG936 in fermentor vessels, and in induction media for SmC are listed in Table 4. The fermentation operating parameters used for control of pH, aeration, and temperature are described in Table 5.

TABLE 4

| Growth Media (g/L) | |
|---|---|
| Amberex 510 Yeast Extract | 35.0 |
| Glycerol | 30.0 |
| (NH$_4$)$_2$SO$_4$ | 5.0 |
| K$_2$HPO$_4$ | 6.0 |
| NaH$_2$PO$_4$ | 3.0 |
| Na Citrate | 1.0 |
| MgSO$_4$ (anhydrous) | 1.7 |
| Trace Elements | 20 ml |
| Ampicillin | 100 µg/ml |
| Kanamycin | 50 µg/ml |
| K-67 | 5 ml/9 liters |
| Induction Media | |
| Glycerol | 100 g |
| NZA-A | 100 g |
| A510 Yeast Extract | 100 g |
| Seed Media (g/L) | |
| NZA-A | 20.0 |
| A510 Yeast Extract | 3.0 |
| Glycerol | 20.0 |
| (NH$_4$)$_2$SO$_4$ | 5.0 |
| K$_2$HPO$_4$ | 6.0 |
| NaH$_2$PO$_4$ | 3.0 |
| Na Citrate | 1.0 |
| MgSO$_4$ (anhydrous) | 1.7 |
| Trace Elements | 20 ml |
| Ampicillin | 100 µg/ml |
| Kanamycin | 50 µg/ml |
| Trace Elements (g/L distilled water) | |
| EDTA (disodium salt) | 5.00 |
| FeCl$_3$.6H$_2$O | 0.50 |
| ZnO | 0.05 |
| CuCl$_2$.2H$_2$O | 0.01 |
| CoNO$_3$.6H$_2$O | 0.01 |
| Ammonium Molybdate | 0.01 |

TABLE 5

| Fermentation Parameters | |
|---|---|
| pH: | 6.7 (controlled with 20% NaOH) |
| Air: | 10 liters/minute (increased if needed) |
| Agitation: | 1000 rpm |
| Temperature: | 28 C. (Growth) |
| | 40 C. (Induction) |
| Back Pressure | 3 psi |
| Dissolved Oxygen | Maintained above 10%. During induction, the fermentor is enriched with oxygen to maintain the Dissolved Oxygen above 10%. |

What is claimed is:

1. A high titer fermentation process for producing Somatomedic C which comprises:
    inoculating an aqueous fermentation medium with a transformed *E. coli* strain containing an expression vector which directs the expression of Somatomedin C under the control of a phage lambda promoter-operator and an expression vector which directs the expression of the cI857 temperature-sensitive repressor protein;
    growing the transformed strain in the fermentation medium for an initial growth period during which the level of dissolved oxygen in the medium is maintained at from about 20 to 60% of saturation and the temperature of the medium is maintained at from about 26° to 30° C.;
    raising the temperature of the fermentation medium to about 40° C. to inactivate the temperature-sensitive protein and initiate an induction period during which Somatomedin C is expressed; and
    allowing the transformant strain to grow and express SmC for the remainder of the induction period while maintaining the level of dissolved oxygen in the medium at from about 10% to 40% of saturation, thereby producing a yield of greater than 900 mg/L of SmC; and
    recovering the Somatomedin C peptide from the transformed cells.

2. The process of claim 1 wherein the transformed strain is lon⁻ and htpR⁻.

3. The process of claim 2 wherein the transformed strain is *E. coli* SG936 (ATCC 53551).

4. The process of claim 1 wherein the temperature is maintained at about 28° C. during the initial growth period.

5. The process of claim 1 wherein the level of dissolved oxygen in the medium is maintained at about 50% of saturation during the initial growth period.

6. The process of claim 1 wherein the initial growth period is from about 14 to 20 hours.

7. The process of claim 1 wherein the initial growth period is about 16 hours.

8. The process of claim 1 wherein the induction period is from about 3 to 8 hours.

9. The process of claim 1 wherein the temperature is increased to about 40° C. to induce production of Somatomedin C when the cell density in the fermentation medium has reached an A$_{550}$ of from 50 to 60.

10. The process of claim 1 wherein nutrients are added to the fermentation medium just before the temperature is raised to begin the induction period.

11. The composition of claim 10 wherein the nutrients contain yeast extract.

12. The composition of claim 10 wherein about 45 to 60 grams of nutrients are added per liter of fermentation medium.

13. The process of claim 12 wherein the nutrients comprise about equal amounts by weight of glycerol, yeast extract, and enzymatic casein hydrolysate.

14. The process of claim 1 wherein the dissolved oxygen level is maintained during the initial growth period by feeding ambient air to the fermentor at a rate of about 0.8 to 1.2 volumes of air (STP) per volume of liquid per minute and mechanically agitating the fermentation medium at about 1,000 rpm with an agitator having a power input of about 0.5 to 2.0 hp per 100 gallons of fermentation medium.

15. The process of claim 14 wherein ambient air is fed to the fermentor at a rate of about 1.0 volume of air per volume of liquid per minute.

16. The process of claim 1 wherein the level of dissolved oxygen during the induction period is maintained at about 10% to 40% of saturation by adding oxygen to the inlet air being fed to the fermentor.

17. The process of claim 16 wherein the dissolved oxygen level is maintained during the induction period by feeding ambient air mixed with oxygen to the fermentor at a rate of about 0.8 to 1.2 volumes of air per volume of liquid per minute and mechanically agitating the fermentation medium at about 1200 rpm with an agitator having hp input of about 0.5 to 2.0 hp per 100 gallons of fermentation medium.

18. The process of claim 17 wherein ambient air is fed to the fermentor at a rate of about 1.0 volume of air per volume of liquid per minute.

* * * * *